United States Patent
Ziche et al.

(10) Patent No.: US 8,314,263 B2
(45) Date of Patent: Nov. 20, 2012

(54) METHOD FOR PRODUCING AMINO-ORGANOSILANES

(75) Inventors: Wolfgang Ziche, Burghausen (DE); Volker Stanjek, Ampfing (DE)

(73) Assignee: Wacker Chemie AG, Munich (DE)

( * ) Notice: Subject to any disclaimer, the term of this patent is extended or adjusted under 35 U.S.C. 154(b) by 332 days.

(21) Appl. No.: 12/671,605

(22) PCT Filed: Jul. 28, 2008

(86) PCT No.: PCT/EP2008/059877
§ 371 (c)(1), (2), (4) Date: Feb. 1, 2010

(87) PCT Pub. No.: WO2009/019161
PCT Pub. Date: Feb. 12, 2009

(65) Prior Publication Data
US 2011/0166373 A1  Jul. 7, 2011

(30) Foreign Application Priority Data
Aug. 7, 2007 (DE) .......................... 10 2007 037 193

(51) Int. Cl.
*C07F 7/18* (2006.01)
(52) U.S. Cl. ....................................... 556/413
(58) Field of Classification Search ........................ None
See application file for complete search history.

(56) References Cited

U.S. PATENT DOCUMENTS

| 3,657,303 | A | * | 4/1972 | Golitz et al. ................... 556/420 |
| 3,673,233 | A | | 6/1972 | Golitz et al. |
| 5,616,755 | A | | 4/1997 | Seiler et al. |
| 6,150,551 | A | | 11/2000 | Kropfgans et al. |
| 6,452,033 | B1 | | 9/2002 | Maki et al. |
| 6,806,379 | B2 | * | 10/2004 | Bauer et al. ................... 556/413 |
| 2002/0042491 | A1 | | 4/2002 | Brader et al. |
| 2006/0194976 | A1 | | 8/2006 | Kornek et al. |
| 2009/0253925 | A1 | | 10/2009 | Kornek et al. |

FOREIGN PATENT DOCUMENTS

| DE | 1812564 A | 6/1970 |
| DE | 19941283 A1 | 5/2000 |
| DE | 10049183 C1 | 7/2002 |
| DE | 102004060627 A1 | 7/2006 |
| EP | 0702017 A1 | 3/1996 |
| GB | 686068 A | 1/1953 |
| JP | 2002293786 A * | 10/2002 |
| WO | 03068780 A1 | 8/2003 |
| WO | 2005047298 A1 | 5/2005 |

OTHER PUBLICATIONS

Voronkov M. G. et al., A novel Synthetic route to 1-AZA-2-Silacyclopentane Derivatives, Journal of Organometallic Chemistry, Elsevier-Sequoia S.A. Lausanne, CH, vol. 406, No. 1 / 02,Mar. 26, 1991, pp. 87-89.

* cited by examiner

*Primary Examiner* — Yevegeny Valenrod
(74) *Attorney, Agent, or Firm* — Brooks Kushman P.C.

(57) ABSTRACT

In the preparation of aminoorganylsilanes and cyclic aminosilanes by reaction of an organyl amine with a haloorganylsilane, the byproduct halide salt of the amine reactant is decomposed to amine by addition of a base whose halide salt forms a liquid phase at a temperature below 200° C., and the liquid base halide is separated from the reaction mixture.

17 Claims, No Drawings

METHOD FOR PRODUCING AMINO-ORGANOSILANES

CROSS-REFERENCE TO RELATED APPLICATION

This application is the U.S. national phase of PCT Appln. No. PCT/EP2008/059877 filed Jul. 28, 2008 which claims priority to German application DE 10 2007 037 193.6 filed Aug. 7, 2007.

BACKGROUND OF THE INVENTION

1. Field of the Invention

The invention relates to a method for producing aminoorganosilanes by reacting an amine with (haloorganyl)silanes.

2. Description of the Related Art

The prior art discloses various methods for producing aminoorganosilanes. The production of amino functional organosilanes is effected predominantly by reacting chlorofunctional organosilanes with very different types of organic amines or ammonia. As a rule, the procedure is such that at least two moles of amine or ammonia are used per mole of chlorofunctional organosilane, so that, in addition to the formation of the aminofunctional organosilane, there is still sufficient amine component available for converting the liberated hydrogen chloride into the corresponding amine hydrochloride or ammonium chloride.

In particular, the high availability of (chloroalkyl)silanes is advantageous. These silanes are obtainable by photochlorination of alkylsilanes or hydrosilylation of halogen-substituted olefins onto Si—H-containing compounds, and are used, for example, as intermediates for the synthesis of a multiplicity of organofunctional silanes. Furthermore, it is possible in this method to rely not only on ammonia but also on a large number of readily available primary and secondary amines for synthesizing the (N-organylaminoorganyl)- and (N,N-diorganylaminoorganyl)triorganylsilanes, which permits a very wide range of use of the method and thereby economical product change in existing industrial manufacturing plants.

GB 686,068 A discloses (amino)-, (N-organylamino)- and (N,N-diorganylaminomethyl)- or (N,N-diorganylaminoethyl)triorganylsilanes. Furthermore, GB 686,068 A describes a method for reacting corresponding (chloromethyl)- or (bromomethyl)triorganosilanes with ammonia, a primary or secondary amine at temperatures of at least 50° C. for the production of the (aminoorganyl)-, (N-organylaminoorganyl)- and (N,N-diorganylaminoorganyl)triorganylsilanes. As a rule, the (chloromethyl)- or (bromomethyl)triorganosilanes are initially introduced into a flask or autoclave, depending on the boiling points of the amine compounds used, and are heated to temperatures above 100° C., preferably 110-130° C. In the case of higher-boiling amines (e.g. cyclohexylamine), the sequence of mixing can be reversed, i.e. the (chloromethyl)- or (bromomethyl)triorganosilanes are added to the heated amine.

According to a method described in DE 1812564 A1, (aminomethyl)silane derivatives are produced by reacting a (chloromethyl)- or (bromomethyl)silane derivative with ammonia or a primary amine. The reaction is effected at temperatures of 80 or 100° C. in a period of 3 or 2 hours, the amine having been initially completely introduced in a molar excess of 1:3.2-6 as early as the beginning of the reaction.

DE 10 2004 060 627 A describes a variation of these methods in which the abovementioned reactions are carried out continuously.

The prior art further discloses methods for reducing halide contents in alkoxysilanes. For example, EP 0702017 A discloses methods based on precipitation of dissolved amine hydrochloride moieties by addition of alkali metal or alkaline earth metal alcoholate salts. An alternative method which is said to permit reduction of chloride content in alkoxysilanes by introduction of ammonia is described in DE 19941283 A1.

A disadvantage of all these methods is the fact that ammonium halides, optionally organically substituted, are formed in quantitative amounts as byproducts and have to be separated off as solids. Separating off such large amounts of solid is time-consuming and hence expensive and moreover requires production plants which have appropriate separation devices, for example powerful and therefore expensive centrifuges. However, this is not the case in many plants—in particular in most multipurpose plants as are typically used for producing fine chemicals.

Here, for example, U.S. Pat. No. 6,452,033 A describes the production of aminoethylaminoorganyltriorganylsilanes by reacting the corresponding chlorofunctional organosilanes with ethylenediamine, the above-mentioned phase separation for separating the hydrochlorides being used in various ways. However, a disadvantage of this method is the fact that it is limited to silanes which have an ethylenediamine unit.

SUMMARY OF THE INVENTION

An object of the invention was to develop a method which no longer has the disadvantages of the prior art. These and other objects have been achieved through an aminoorganyltriorganylsilane production method which haloorganyl silane and amine are reacted, and base is added to form a halide of the base, liberating amine reactant from the amine hyrochloride byproduct, and separating the halide of the base in liquid form.

DETAILED DESCRIPTION OF THE PREFERRED EMBODIMENTS

The invention thus relates to a method for producing aminoorganyltriorganylsilanes of the general formula (1)

by reacting cyclic or acyclic amines of the general formula (2),

with (haloorganyl)silanes of the general formula (3)

in which
R' is an acyloxy radical or an alkoxy radical having in each case 1-10 C atoms,
R$^1$ is a hydrocarbon radical having 1-10 C atoms,
R$^2$ is a divalent hydrocarbon radical having 1-10 C atoms,
R$^3$, R$^4$, independently of one another, are hydrogen or a hydrocarbon radical having 1-10 C atoms, it being possible for R$^3$, R$^4$ to be linked to one another and for the resulting ring also to contain further heteroatoms, NH groups or NR$^{2a}$ groups,
R$^{2a}$ divalent hydrocarbon radical having 1-10 C atoms,
n is a number equal to 0, 1, 2 or 3 and
X is chlorine, bromine or iodine,
the reaction comprising the following steps:
a) reaction of the (haloorganyl)silane of the general formula (3) and of the amine of the general formula (2) at a temperature of from 0 to 250° C., the ammonium halide of the amine of the general formula (2) being formed as a byproduct in addition to the silane of the general formula (1),
b) addition of a base (B), complete or partial double decomposition occurring in which the amine of the general formula (2) is liberated again and the halide of the base (B) forms, the halide of the base (B) being liquid at temperatures of not more than 200° C., and
c) removal of the resulting liquid halide of the base (B).

The ammonium halide of the amine of the general formula (2) is typically precipitated as an insoluble solid which dissolves again step b) after the addition of the base (B), resulting in the formation of a separate liquid phase which substantially contains the halide of the base (B) and is then removed in step c).

Based on (haloorganyl)silane of the general formula (3), the amine of the general formula (2) is preferably used in excess, i.e. in molar ratios of from 1.1:1 to 100:1, more preferably from 1.5:1 to 50:1, yet more preferably from 2:1 to 20:1, and in particular from 3:1 to 10:1. Based on silane of the general formula (3), the base (B) is preferably used in molar ratios of from 0.5:1 to 10:1, more preferably from 0.7:1 to 5:1, yet more preferably from 0.8:1 to 2:1, and in particular from 0.9:1 to 1.0:1.

The hydrocarbon radicals $R^1$, $R^2$, $R^{2a}$, $R^3$, $R^4$ may be saturated or unsaturated, branched or straight-chain, substituted or unsubstituted.

The hydrocarbon radicals $R^1$, $R^3$, $R^4$ may be alkyl radicals such as the methyl, ethyl, n-propyl, isopropyl, 1-n-butyl, 2-n-butyl, isobutyl, tert-butyl, n-pentyl, isopentyl, neopentyl, or tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl, and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as the o-, — and p-tolyl radicals, xylyl radicals and ethylphenyl radicals; and aralkyl radicals such as the benzyl radical, and the alpha- and the beta-phenylethyl radicals; and combinations thereof linked by heteroatoms such as N, O, S, P. The hydrocarbon radicals $R^1$, $R^3$, $R^4$ preferably have 1-6, in particular 1-3, C atoms. Preferably, $R^1$ is a methyl, ethyl, isopropyl, n-propyl, isobutyl, n-butyl, pentyl, hexyl, heptyl, octyl, nonyl, decyl, phenyl, benzyl, or allyl radical.

The radicals $R^3$ and $R^4$ are preferably selected from the preferred radicals of $R^1$ and furthermore from hydrogen or cyclohexyl or phenyl radicals. Preferably, not more than one of the radicals $R^3$ or $R^4$ is hydrogen. In a particularly preferred embodiment, the radical $R^3$ is a phenyl or cyclohexyl radical and the radical $R^4$ is hydrogen.

Furthermore, the radicals $R^3$ and $R^4$ may be linked directly or by heteroatoms so that, with the structural inclusion of the N atom, cyclic structures $-NR^3R^4$ result. Preferably, the cyclic structures $-NR^3R^4$ have 5 to 10 ring atoms, in particular 5, 6 or 8 ring atoms. Examples of these are the morpholino, piperidino, and pyrrolidino radicals, which are also preferred. Moreover, the radical $-NR^3R^4$ is preferably the N,N-bis(N',N'-dimethylaminopropyl) radical.

The radical R' preferably has the meaning of $OR^1$. Preferably, R' is a methoxy, ethoxy, isopropoxy, n-propoxy, butoxy, phenoxy, benzyloxy or allyloxy radical.

The radicals $R^2$ and $R^{2a}$ are preferably a divalent hydrocarbon radical having 1-6 C atoms, in particular a methylene, ethylene or propylene group, most preferably the methylene group.

The radical X is preferably chlorine or bromine, in particular chlorine.

n preferably has the value 1, 2 or 3.

The invention furthermore relates to a method for producing cyclic aminosilanes of the general formula (4)

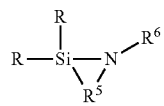
(4)

by reacting amines of the general formula (5), $$H_2NR^7 \qquad (5)$$

with (haloorganyl)silanes of the general formula (6)

$$(R_2)Y^1Si-R^5-Y^2 \qquad (6),$$

in which
$R^5$ is a divalent hydrocarbon radical having 1-10 C atoms in which the hydrocarbon chain may be interrupted by carbonyl groups, carboxyl groups, oxygen atoms, NH or $NR^8$ groups,
$R^6$ is hydrogen or a hydrocarbon radical having 1-10 C atoms which may be substituted by halogen atoms, OH groups and $-NH_2$, $-NHR^8$, $NR^8_2$ groups,
$R^7$ is hydrogen or a hydrocarbon radical having 1-10 C atoms which may be substituted by halogen atoms, OH groups and $-NH_2$, $-NHR^8$, $NR^8_2$ groups,
R is a hydrocarbon radical, an acyloxy radical or an alkoxy radical having in each case 1-10 C atoms,
$R^8$ is a hydrocarbon radical having 1-10 C atoms, and
$Y^1$ and $Y^2$ are chlorine, bromine or iodine,
the reaction comprising the following steps:
a) reaction of the (haloorganyl)silane of the general formula (6) and of the amine of the general formula (5) at a temperature of from 0 to 300° C., the amine of the general formula (5) being used with a 1.1- to 1000-fold excess and the ammonium halide of the amine of the general formula (5) being formed as a byproduct in addition to the silane of the general formula (4),
b) addition of a base (B), complete or partial double decomposition occurring, in which the amine of the general formula (5) is liberated again and the halide of the base (B) forms, the halide of the base (B) being liquid at temperatures of not more than 200° C., and
c) removal of the resulting liquid halide of the base (B).

In this variant of the method according to the invention, too, ammonium chloride of the amine of the general formula (5) is typically precipitated as an insoluble solid, which dissolves again step b) after the addition of the base (B), resulting in the formation of a separate liquid phase which substantially contains the halide of the base (B) and is then separated off in step c).

$R^5$, $R^6$ and $R^7$ may be saturated or unsaturated, branched or straight-chain, substituted or unsubstituted.

Preferably, $R^5$ is a propylene or butylene group.

$R^6$ is preferably hydrogen or a cyclic or linear alkyl radical having 1-6 carbon atoms or a 3-aminopropyl radical. $R^7$ is preferably hydrogen or a cyclic or linear alkyl radical having 1-6 carbon atoms.

The examples and preferred radicals stated for R' and $R^1$ are also examples and preferred radicals for R.

The examples and preferred radicals stated for $R^1$ are also examples and preferred radicals for $R^8$.

The radicals $Y^1$ and $Y^2$ are preferably chlorine or bromine, in particular chlorine.

In a particularly preferred embodiment of the invention, the aminosilane of the general formula (5) is N-((3-aminopropyl)dimethylsilyl)-2,2-dimethyl-1-aza-2-silacyclopentane. In this case, the product in step a) is preferably formed from 2 molecules of chlorosilane in which $R^5$ is propylene, R is methyl and $Y^1$ and $Y^2$ are chlorine and 2 ammonia molecules, 4 molecules of ammonium chloride forming.

Based on the silane of the general formula (6), the amine of general formula (5) is preferably used in excess, i.e. in molar ratios of from 1.2:1 to 1000:1, more preferably from 1.6:1 to 100:1, yet more preferably from 2:1 to 10:1, and in particular from 3:1 to 6:1. Based on the silane of the general formula (6), the base (B) is preferably used in molar ratios of from 0.5:1 to 10:1, more preferably from 0.7:1 to 5:1, yet more preferably from 0.8:1 to 2:1, and in particular from 0.9:1 to 1.0:1.

In principle, the steps a) and b) can be effected in succession or simultaneously. Also conceivable is a time-lapsed procedure, beginning with step b), i.e. the addition of the oligoamine, that is to say after the beginning but still before the end of step a). If a base (B) which has free NH or $NH_2$ groups is used in the method according to the invention, step b), i.e. the addition of the oligoamine, is however preferably effected after the reaction in step a) is complete. Preferably used bases (B) are those which, in step b) of the method, form salts which form liquids at temperatures as low as <150° C., more preferably <100° C. or <90° C.

Step a) of the method according to the invention is preferably carried out at temperatures of from 50 to 250° C. In order to achieve a compromise between economically expedient reaction times and a reaction leading to as few byproducts as possible, temperatures of from 50 to 220° C., in particular from 80° C. to 150° C., have proven particularly advantageous. Since step a) is generally exothermic, it is preferably carried out with cooling.

The steps b) and c) of the method are preferably carried out at temperatures of 0-250° C., more preferably at temperatures of from 20 to 150° C. and most preferably at temperatures of from 50 to 100° C. Preferably, the temperature remains constant during the steps b) and c) preferably within a temperature frame of 30° C., more preferably 20° C. Since step b) is generally exothermic, it is preferably carried out with cooling.

All reaction steps are preferably carried out under inert gas, e.g. nitrogen and argon.

In a preferred embodiment of the invention, the methods according to the invention may also have one or more of the following additional steps:

a1) if the amine of the general formulae (2) and (5) was used in excess in step a), this excess can be completely or partly separated off even before the addition of the base (B) in step b). Separating off is preferably effected by distillation. This measure preferably serves for reducing the solubility of the respective salt or salts in the organic phase.

d) addition of one or more nonpolar solvents (L) to the product-containing phase. The additional solvent (L) can be added before, during or after the steps a), a1), b) and c) of the method. This measure preferably serves for reducing the solubility of the respective salt or salts in the organic phase. If the addition of the nonpolar solvent is effected after step c) of the method, the salts precipitated in this step are preferably separated off in an additional separation step, for example a filtration. The amounts of salt to be separated off are, however, extremely small compared with the original amount of salt in step c), and the removal is correspondingly simple. If the addition of the nonpolar solvent is effected before or during the step c), the respective salts are displaced from the product phase into the liquid phase, which substantially comprises the halide of the base (B), and are separated off together with the halide.

e) Distillative separation or purification of the product (1) or (4) and of the amine (2) or (5) optionally used in excess in step a) and liberated in the double decomposition in step b). In this fractional distillation, the amine of the general formulae (2) and (5) is preferably obtained directly in sufficiently high purity so that it and can be reused without further working-up in the next reaction cycle. The product of the general formulae (1) and (4) is also preferably obtained directly in sufficient purity in the corresponding distillation. If, in the phase separation in step e), halides of the base (B) remain the organic phase, these are preferably likewise separated by distillation. The same applies to the solvent (L) optionally additionally added in step d).

It is possible for all components, in particular product of the general formulae (1) and (4), amine of the general formulae (2) and (5) and optionally the base (B) and the solvent (L), to be separated from one another by a single fractional distillation. This can also be effected by a plurality of separate distillation steps. Thus, for example, initially only the amine of the general formulae (2) and (5) can be removed by distillation, the crude product initially remaining in the bottom product of the distillation and then being purified in a separate distillation or thin-film evaporation step.

f) Additional addition of ammonia to the product-containing phase after the phase separation in step c) and removal of the resulting ammonium halide. This measure can be suitable in particular for reducing the halide content in the end product.

g) Additional addition of alkali metal alcoholates, preferably sodium or potassium alcoholates, to the product-containing phase after the phase separation in step c) and removal of the resulting alkali metal halides. This measure may be suitable in particular for reducing the halide content in the end product.

h) Addition of additional polymeric polyamines to the product-containing phase after the phase separation in step c). This measure may serve for binding any residues of ionic halides so that these substantially remain behind in the bottom product of the distillation in a final distillation of the product of the general formulae (1) and (4) (cf. step e) and a correspondingly low-halide product is obtained.

i) Recovery or recycling of the amine of the general formulae (2) and (5) which is optionally used in excess in step a) and of the amine of the general formulae (2) and (5) which is liberated in step b). If the amine of the general formulae (2) and (5) cannot be obtained, entirely or at least in parts, in sufficient purity by simple distillation—cf. step e)—the interfering products, byproducts or residues of the base (B) added in step b) can be separated off by one or more further purification steps. The following may be mentioned here by way of example further distillative purification steps of the amine fractions still not sufficiently pure after the first distillation (step e))

additional addition of aliphatic ketones or aldehydes to the product-containing phase after step c) or to the amine fractions distilled under step e). This measure can—if the base (B) added in step b) comprises compounds having primary amino groups—serve for converting residues of the base (B) still present in these phases into the corresponding imines. The latter can often be more easily separated off by distillation from the products and especially from the amines of the general formulae (2) and (5) used in excess and/or liberated again step b) than the base (B) itself.

l) Recovery of the base (B) used in step b), preferably by double decomposition of the resulting halide of this base with strong bases, e.g. alkali metal or alkaline earth metal hydroxides, carbonates, bicarbonates, etc. The respective bases can be used as such or in aqueous or nonaqueous solution or suspension. If aqueous solutions are used and/or water is liberated in the reaction, this is preferably separated off by distillation from the base (B). If ethylenediamine was used as base (B), this distillative separation is preferably effected at such high pressure that ethylenediamine and water no longer form an azeotrope.

If the base (B) is a compound, for example an amine, which is itself reactive toward the silane of the general formulae (3) and (6), the amine of the general formulae (2) and (5) is preferably purified by said steps of the method to such an extent that the content of the base (B) in the amines of the general formulae (2) and (5) is below 3%, preferably below 1% and in particular below 0.5%.

In a particularly preferred combination of the described variants of the method according to the invention, the amine of the general formulae (2) and (5) is used in excess, the excess amine first being removed substantially or at least in parts by distillation by a step a1). Thereafter, a solvent (L) (step d)) and the base (B) are optionally added (step b)) and the salt phase is separated off (step d)). Thereafter, the solvent (L)—if present—and the amine of the general formulae (2) and (5) which is liberated in step b) are removed by distillation (step e)). Both the solvent (L) and both distillates of the amine of the general formulae (2) and (5) are preferably obtained in such high purity that they are directly reused without further purification.

In a further particularly preferred variant, a solvent (L) whose boiling point is below that of the amine of the general formulae (2) and (5) but above the boiling point of the base (B) is used in step d), so that any residues of the base (B) which are present in the organic phase can be removed together with the solvent (L) and then an amine of the general formulae (2) and (5) can be obtained by distillation (step e)), that contains above the preferred low content of the base (B).

Of course, the method can be carried out both batchwise, for example in stirred tanks, and continuously. The latter, for example, by effecting steps a), b) and optionally further steps (see above) in a tubular reactor or a stirred vessel cascade. The individual substances are metered in or mixed in together or—preferably—in succession. Suitable methods, for example with the use of settling vessels, decanters, etc., are known and are widely described in the literature also for the subsequent continuous phase separation (step c).

Preferably, the water content of the amines of the general formulae (2) and (5) which are used is from 0 to 20,000 ppm, more preferably from 0 to 5000 ppm, and most preferably from 0 to 1000 ppm.

The $pK_b$ value of the amines of the general formulae (2) and (5) which are to be used is preferably greater than that of the base (B), more preferably at least 1 $pK_b$ unit greater, most preferably 2 $pK_b$ units greater.

In a preferred embodiment, compounds whose boiling point differs both from the product (1) or (4) and from the amine of the general formulae (2) and (5) by at least 40° C., more preferably by at least 60° C. and most preferably at least 90° C. are chosen as base (B), so that residues of base (B) which remain the organic phase in the phase separation in step c) can be separated off sufficiently well by distillation both from the product of the general formulae (1) and (4) and from the amine of the general formulae (2) and (5).

Oligoamines (O) containing ethylene- or propylenediamine units are preferably used as base (B). Preferably, the oligoamines (O) contain from 1 to 20, in particular from 1 to 10, ethylene- or propylenediamine units. Preferred oligoamines (O) are ethylenediamine, diethylenetriamine, diazabicyclooctane, pentamethyldiethylenetriamine, propylenediamine, and N4-amine (BASF AG).

Ethylenediamine is particularly preferably used as base (B). Thus, ethylenediamine shows the following surprising combination of properties in the method according to the invention:

The addition of ethylenediamine leads in step b) to substantially complete double decomposition even when only the most preferred amount of ethylenediamine of from 0.8 to 2 equivalents, based on the amount of the (haloorganyl)silane of the general formulae (3) and (6), is added.

The salt phase obtained by the substantial double decomposition has a melting point of about 80° C.

The liquid salt phase separates completely from the organic phase after only a few minutes and can therefore be separated off without a large and hence expensive time requirement for a phase separation.

With the method according to the invention, aminoorganyltriorganylsilanes of the general formula (1) and cyclic aminosilanes of the general formula (4) can be obtained in a simple manner in good to very good yields. The methods can be implemented on an industrial scale easily and without danger.

The purity of the aminoorganyltriorganylsilanes of the general formula (1) and cyclic aminosilanes of the general formula (4) which are produced according to the invention is preferably at least 85%, more preferably at least 95%. This purity can be increased to more than 95% by means of an optional downstream distillation step e) of the product.

This purity can be increased to more than 95% by means of an optional downstream distillation step e) of the product.

Compared with the prior art, the method according to the invention has the advantage that the main proportion of the ammonium salts of the amines of the general formulae (2) and (5), which form as a byproduct, no longer need to be separated off as a solid, which is generally complicated and expensive on the industrial scale, in particular in the case of poorly crystallizing ammonium salts (for example the ammonium salts of aniline). In addition, many so-called multipurpose plants do not have sufficiently efficient plant elements (e.g. centrifuges) for separating such large amounts of solid. As a result of the double decomposition, two liquid phases can now be separated from one another in a simple manner. Moreover, additional steps of washing the filter cake with solvent are unnecessary. At the same time, the formation of byproducts can be significantly reduced by the use of optimized excesses of amine according to the general formulae (2) and (5). Moreover, it is remarkable that the method according to the invention is suitable for recovering the often comparatively expensive amines of the formulae (2) and (5) which would be consumed in step a) for the formation of the corresponding ammonium salts, by the double decomposition with the generally relatively economical base (B), e.g. ethylenediamine, and thereby making these amines accessible for reuse.

All above symbols of the above formulae have their meanings in each case independently of one another. In all formulae, the silicon atom is tetravalent.

In the following examples, unless stated otherwise in each case, all stated amounts and stated percentages are based on weight and all pressures are 0.10 MPa (abs.).

WORKING EXAMPLES

Example 1

Production of 4-(triethoxysilylmethyl)tetrahydro-1,4-oxazine 82 g of dry morpholine ($pK_b$ 5.67) were heated to 120° C. in a 500 ml four-necked flask having a reflux condenser, KPG stirrer and thermometer and 80 g of chloromethyltriethoxysilane were added in the course of 180 min with stirring. After the end of the addition, the temperature was reduced to 105° C. and 56.6 g of ethylenediamine ($pK_b$ 4.07) were added to the mixture in the course of 10 min with stirring, phase separation occurring. At constant temperature, stirring was effected for a further 30 min and the heavier ethylenediamine hydrochloride phase was then separated off. The upper phase was subjected to fractional distillation. 68 g (yield 68%) of 4-(triethoxysilylmethyl)tetrahydro-1,4-oxazine were obtained, the purity of which was determined as 98.4% by gas chromatography.

Example 2

Production of 4-(triethoxysilylmethyl)tetrahydro-1,4-oxazine 82 g of dry morpholine ($pK_b$ 5.67) were heated to 120° C. in a 500 ml four-necked flask having a reflux condenser, KPG stirrer and thermometer and 80 g of chloromethyltriethoxysilane were added in the course of 180 min with stirring. After the end of the addition, the temperature was reduced to 105° C. and 226.6 g of ethylenediamine ($pK_b$ 4.07) were added to the mixture in the course of 10 min with stirring, phase separation occurring. At constant temperature, stirring was effected for a further 30 min and the heavier ethylenediamine hydrochloride phase was then separated off. The upper phase was subjected to fractional distillation without a distillation column. 37 g (45% recovery) of morpholine having a purity of 89.7% and 73.5 g (yield 74.2%) of 4-(triethoxysilylmethyl)-tetrahydro-1,4-oxazine were obtained, the purity of which was determined as 97.3%.

Example 3

Recycling of an Amine Liberated in the Double Decomposition

In the procedure corresponding to Example 2, morpholine is liberated in the double decomposition and can be separated off as a separate fraction in the final fractional distillation. The morpholine fraction obtained contains 0.9% of ethylenediamine and 0.45% of tetraethyl silicate according to gas chromatographic analysis. Based on the ethylenediamine content, 4 mole equivalents of methyl ethyl ketone and 1 mole equivalent of additional tetraethyl silicate are added to the morpholine. After further distillation, morpholine having a purity of 98.9% and having an ethylenediamine content of 0.06% is obtained.

Example 4

Production of N-phenylaminomethyltriethoxysilane

In a 500 ml four-necked flask having a reflux condenser, KPG stirrer and thermometer, 65.7 g of dry aniline ($pK_b$ 9.4) were heated to 120° C. and 60 g of chloromethyltriethoxysilane were added in the course of 180 min with stirring and stirring was effected for a further 60 min. Thereafter, the temperature was reduced to 105° C. and 42.4 g of ethylenediamine ($pK_b$ 4.07) were added to the mixture in the course of 10 min with stirring, phase separation occurring. At constant temperature, stirring was effected for a further 30 min, cooling to 70° C. being effected during this procedure and the heavier ethylenediamine hydrochloride phase then being separated off. The upper phase was subjected to fractional distillation without a distillation column. 18.3 g of aniline having a purity of 84.8%, 14.4 g of aniline having a purity of 97.8% (45% recovery) and 47.8 g (yield 62.9%) of N-phenylaminomethyltriethoxysilane were obtained, the purity of which was determined as 88.9%. The chloride value of the product was 88 ppm.

Example 5

Production of N-phenylaminomethyltriethoxysilane

In a 1000 ml four-necked flask having a reflux condenser, KPG stirrer and thermometer, 602 g of dry aniline ($pK_b$ 9.4) were heated to 120° C. and 200 g of (chloromethyl)triethoxysilane were added in the course of 180 min with stirring and stirring was effected for a further 60 min. Thereafter, the temperature was reduced to 105° C. and 109 g of ethylenediamine ($pK_b$ 4.07) were added to the mixture in the course of 10 min with stirring, phase separation occurring. At constant temperature, stirring was effected for a further 30 min, cooling to 70° C. being effected and the heavier ethylenediamine hydrochloride phase then being separated off. 27 g of anhydrous Lupasol G20 (BASF AG) are then added to the upper phase and distilled as described in Example 4. 200 g of N-phenylaminomethyltriethoxysilane (73.2% yield) having a purity of 94.9% are obtained. The chloride value was 8 ppm.

Example 6

Production of N-phenylaminomethyltrimethoxysilane

In a 4 l four-necked flask having a bottom valve, KPG stirrer, reflux condenser, dropping funnel and thermometer, 2179.3 g of aniline ($pK_b$ 9.4) were initially introduced under inert gas (argon) and heated to about 120° C. with stirring. Thereafter, 800.38 g of chloromethyltrimethoxysilane were metered in the course of about 1.5 h, a white solid being precipitated. The temperature was kept at 120-130° C. during this procedure. After further stirring for two hours at the same temperature, the reaction mixture was cooled to about 90° C. and 337.52 g of ethylenediamine ($pK_b$ 4.07) were metered in the course of 30-45 min. In the course of a slightly exothermic reaction, the solid dissolved and an emulsified two-phase system forms, which is stirred for a further 15 min at 90° C.

After the stirring is stopped, the phases separate completely in the course of about 10 min. Thereafter, the lower salt phase (ethylenediamine hydrochloride) is discharged through the bottom valve at 90° C.

The aniline is distilled off from the remaining solution in two fractions at a pressure of 20 mbar over a 30 cm Vigreux column, a white solid once again being precipitated in the bottom. Once again, 31.8 g of ethylenediamine were added dropwise, a liquid salt phase forming again, which was separated off in the liquid state.

11.13 g of anhydrous Lupasol G20 (BASF AG) were added to the crude product. Thereafter, the product was subjected to precision distillation at 1 mbar over a 30 cm Vigreux column, 765.5 g of N-phenylaminomethyltrimethoxysilane (71.8% yield) having a purity of 97.6% being obtained. The chloride content in the product was 11 ppm.

Example 7

Production of N-phenylaminomethyltrimethoxysilane

In a 4 l four-necked flask having a bottom valve, KPG stirrer, reflux condenser, dropping funnel and thermometer, 2179.3 g of aniline ($pK_b$ 9.4) were initially introduced under inert gas (argon) and heated to about 120° C. with stirring. Thereafter, 800.38 g of chloromethyltrimethoxysilane were metered in the course of about 1.5 h, a white solid being precipitated. During this procedure, the temperature was kept at 120-130° C. After further stirring for two hours at the same temperature, the reaction mixture was cooled to about 110° C. At this temperature and a pressure of 20 mbar, 1140 g of aniline were distilled off. The suspension remained readily stirrable. The purity of the aniline distilled off was about 98% and it can be used without further purification in a further synthesis cycle.

Thereafter, 580 g of xylene (technical mixture) are added. The suspension cools to a temperature of about 80° C. during this procedure. Thereafter, 337.52 g of ethylenediamine ($pK_b$ 4.07) were metered in over the course of 15 min. During the slightly exothermic reaction (the reaction mixture heats up to about 100° C.), the solid dissolved and an emulsified two-phase system forms, which is further stirred for 15 min at 90° C.

After the stirring had stopped, the phases separated completely in the course of about 10 min. Thereafter, the lower salt phase (ethylenediamine hydrochloride) was discharged through the bottom valve at 90° C.

The xylene was distilled off from the remaining solution at a pressure of about 30 mbar over a 30 cm Vigreux column. The resulting xylene fraction (about 600 g) also contained about aniline (about 10% and ethylenediamine residues (about 4%) in addition to xylene (about 82%). This xylene can be reused without further working-up in the next synthesis cycle in spite of the impurities.

Thereafter, the aniline was distilled off in 2 fractions at a pressure of 20 mbar over a 30 cm Vigreux column. About 380 g of aniline having a purity of >98% were obtained, which contain less than 0.1% of ethylenediamine and can be used without further working-up in a further synthesis cycle just like the first aniline fraction. 11.13 g of anhydrous Lupasol G20 (BASF AG) were added to the crude product obtained. Thereafter, the product was subjected to precision distillation at 1 mbar over a 30 cm Vigreux column, 830 g of N-phenylaminomethyltrimethoxysilane (77.8% yield) having a purity of 97.5% being obtained. The chloride content in the product was 14 ppm.

Example 8

Production of N-((3-aminopropyl)dimethylsilyl)-2,2-dimethyl-1-aza-2-silacyclopentane The chemical synthesis of N-((3-aminopropyl)dimethylsilyl)-2,2-dimethyl-1-aza-2-silacyclopentane—i.e. step a) of the method according to the invention—was carried out in an autoclave as described in DE 100 49 183, example 1, paragraph [0020], the 3-chloropropyldimethylchlorosilane used as starting material having been reacted substantially quantitatively with ammonia ($pK_b$ 4.77) to give the desired product. The only difference compared with the method described in the abovementioned paragraph was that the resulting suspension of N-((3-aminopropyl)dimethylsilyl)-2,2-dimethyl-1-aza-2-silacyclopentane and ammonium hydrochloride was taken up not with pentane but with n-heptane.

For further working-up, the suspensions from a plurality of autoclave batches were combined. The combined suspension contained about 362.5 g (1.575 mol) of product, 337.85 g (6.316 mol of ammonium chloride and 1812.5 g of n-heptane. It was heated to 90° C. At this temperature, 378.45 g (6.2970 mol) of ethylenediamine ($pK_b$ 4.07) were metered in. An emulsified two-phase system formed after a few minutes and was further stirred for 1 h at 90° C.

After stirring had ceased, the phases separated completely in the course of about 10 min. Thereafter, the heavier ethylenediamine hydrochloride phase was separated off. The upper, organic phase was transferred to an apparatus having a short distillation bridge and the solvent n-heptane was removed at atmospheric pressure by distillation. Thereafter, the crude product was subjected to precision distillation in vacuo over a 30 cm Vigreux column. 275 g of N-((3-aminopropyl)dimethylsilyl)-2,2-dimethyl-1-aza-2-silacyclopentane having a purity of >95% were obtained.

The invention claimed is:

1. A method for preparing aminoorganyltriorganylsilanes of the formula (1)

comprising reacting cyclic or acyclic amines of the formula (2),

with (haloorganyl)silanes of the formula (3)

in which

R' is a $C_{1-10}$ acyloxy radical or $C_{1-10}$ alkoxy radical, $R^1$ is a $C_{1-10}$ hydrocarbon radical, $R^2$ is a $C_{1-10}$ divalent hydrocarbon radical, $R^3$, $R^4$, independently of one another, are hydrogen or a $C_{1-10}$ hydrocarbon radical, wherein $R^3$ and $R^4$ are optionally linked to one another to form a ring structure, the ring structure optionally containing heteroatoms, n is 0, 1, 2 or 3, and X is chlorine, bromine or iodine, the step of reacting comprising the following steps:

a) reacting the (haloorganyl)silane of the formula (3) and the amine of the formula (2) at a temperature of from 0 to 250° C., an ammonium halide of the amine of the formula (2) being formed as a byproduct in addition to aminoorganyltriorganylsilane of the formula (1), b) adding a base (B), as a result of which amine of the formula (2) is liberated and a halide of the base (B) forms, the halide of the base (B) being liquid at a temperature of not more than 200° C., and c) removing the halide of the base as a liquid from a phase containing the aminoorganyltriorganylsilanes.

2. The method of claim 1, wherein not more than one of the radicals $R^3$ or $R^4$ is hydrogen.

3. A method for preparing cyclic aminosilanes of the formula (4)

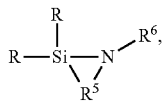
(4)

comprising reacting amines of the formula (5),

(5)

with (haloorganyl)silanes of the formula (6)

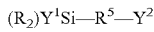
(6), in which
$R^5$ is a divalent $C_{1-10}$ hydrocarbon radical in which the hydrocarbon chain is optionally interrupted by carbonyl groups, carboxyl groups, oxygen atoms, NH or $NR^8$ groups,
$R^6$ is hydrogen or a $C_{1-10}$ hydrocarbon radical optionally substituted by halogen atoms, OH groups, $-NH_2$, $-NHR^8$, or $NR^8_2$ groups,
$R^7$ is hydrogen or a $C_{1-10}$ hydrocarbon radical optionally substituted by halogen atoms, OH groups, $-NH_2$, $-NHR^8$, or $NR^8_2$ groups,
R is a $C_{1-10}$ hydrocarbon radical, a $C_{1-10}$ acyloxy radical, or a $C_{1-10}$ alkoxy radical,
$R^8$ is a $C_{1-10}$ hydrocarbon radical, and
$Y^1$ and $Y^2$ are chlorine, bromine or iodine,
the step of reacting comprising the following steps:
a) reacting the (haloorganyl)silane of the formula (6) and the amine of the formula (5) at a temperature of from 0 to 300° C., the amine of the formula (5) being present in a 1.1 to 1000 molar excess and an ammonium halide of the amine of the formula (5) being formed as a byproduct in addition to the cyclic aminosilane of the formula (4),
b) adding a base (B), as a result of which the amine of the formula (5) is liberated and a halide of the base (B) forms, the halide of the base (B) being liquid at a temperature of not more than 200° C., and
c) removing the halide of the base (B) as a liquid from a phase containing the cyclic aminosilane.

4. The method of claim 1, wherein X is chlorine.

5. The method of claim 3, wherein $Y^1$ and $Y^2$ are chlorine.

6. The method of claim 1, wherein the base (B) forms hydrohalides in step b) which form a liquid phase at a temperature below 150° C.

7. The method of claim 3, wherein the base (B) forms hydrohalides in step b) which form a liquid phase at a temperature below 150° C.

8. The method of claim 1, wherein oligoamines which have 1 to 20 ethylene- or propylenediamine units are used as a base (B).

9. The method of claim 3, wherein oligoamines which have 1 to 20 ethylene- or propylenediamine units are used as a base (B).

10. The method of claim 1, in which ethylenediamine is used as base (B).

11. The method of claim 3, in which ethylenediamine is used as base (B).

12. The method of claim 1, wherein unreacted amine of the formula (2) which is liberated by the addition of the base (B) is separated from a reaction mixture which results following separation of a liquid phase comprising the halide of the base (B), and is used as a source of amine of the formula (2) in the method.

13. The method of claim 3, wherein unreacted amine of the formula (5) which is liberated by the addition of the base (B) is separated from a reaction mixture which results following separation of a liquid phase comprising the halide of the base (B), and is used as a source of amine of the formula (5) in the method.

14. The method of claim 12, further comprising treating the liquid phase comprising the halide of the base (B) with a base stronger than the basicity of base (B) to liberate base (B), separating base (B) by distillation, and reusing the base (B) thus separated in a further reaction according to the method.

15. The method of claim 13, further comprising treating the liquid phase comprising the halide of the base (B) with a base stronger than the basicity of base (B) to liberate base (B), separating base (B) by distillation, and reusing the base (B) thus separated in a further reaction according to the method.

16. The method of claim 1, wherein the $pK_b$ of the amine of formula (2) is at least 1 $pK_b$ unit greater than the $pK_b$ of the base (B).

17. The method of claim 3, wherein the $pK_b$ of the amine of formula (5) is at least 1 $pK_b$ unit greater than the $pK_b$ of the base (B).

* * * * *